United States Patent [19]

Lintott

[11] Patent Number: Plant 7,380

[45] Date of Patent: Nov. 13, 1990

[54] CHRYSANTHEMUM PLANT NAMED EARLY FRESCO

[75] Inventor: Keith G. Lintott, Sussex, England

[73] Assignee: Framptons Nurseries Ltd., West Sussex, England

[21] Appl. No.: 164,228

[22] Filed: Mar. 4, 1988

[51] Int. Cl.[5] ..... A01H 5/00

[52] U.S. Cl. ..... Plt./77

[58] Field of Search ..... Plt./77

*Primary Examiner*—Robert E. Bagwill

*Attorney, Agent, or Firm*—Brisebois & Kruger

[57] ABSTRACT

A new variety of *Chrysanthemum morifolium* Bailey of the white spray type, known as "Early Fresco" and characterized by a long flowering season, fast response, vigorous growth, and non-susceptibility to tip scorch-/loss.

1 Drawing Sheet

This invention relates to a new and distinct variety of *Chrysanthemum morifolium* bailey (spray type) known as "Early Fresco".

My new variety "Early Fresco" is a white sport from the variety White Fresco. White Fresco resulted from an extensive breeding program to produce improved varieties for year round Chrysanthemum production, particularly for winter production. White Fresco is a white sport found in the variety Pink Fresco, which originated from a cross between the variety Rosechip and the variety Artic, the former being the seed parent and the latter being the pollen parent.

The variety Pink Fresco resulted from an extensive breeding program to produce improved varieties for year round Chrysanthemum production, particularly for winter production.

I discovered the mutation known as "Early Fresco" in 1985, in a nursery in Chichester, West Sussex, England.

Early Fresco has the following improved characteristics over the variety White Fresco, the most similar year round spray type grown in Britain.

1. Early Fresco has a long flowering season similar to White Fresco.
2. Early Fresco is not susceptible (very resistant) to tip scorch/loss.
3. The response of Early Fresco is faster than White Fresco.
4. More vigorous than White Fresco, but Early Fresco does not stretch to produce long pedicels requiring growth regulator treatment.
5. The flower size of Early Fresco is similar to White Fresco.

Asexual production of this new variety "Early Fresco" as performed in Sussex, England, by rooting vegatative shoots shows that the above characteristics are fixed and come true to type through succeeding generations.

The accompanying drawing shows a typical flower of my new variety depicted in color as nearly true as it is reasonably possible to make the same in a color illustration of this type.

The following is a detailed description of the new variety "Early Fresco" with color terminology in accordance with The Royal Horticultural Society Colour Chart, (R.H.S.).

Genus: Chrysanthemum.

Species: Morifolium Bailey.

Type: Spray.

Class: Decorative.

Breeding: A cultivated sport or mutation of "White Fresco" which was a sport found in the variety "Pink Fresco" which was a cross between the variety "Rosechip" and the variety Artic, the former being the seed parent and the latter being the pollen parent.

Propagation: Holds its distinguishing characteristics through succeeding propagations by rooting vegetative shoots.

Flower: As grown and observed in Sussex, England, 6 to 12 flowers are borne on pedicels, after removal of the main apical bud.

Bloom:

*Size.*—Diameter of 7.5 cm. to 9.5 cm. when fully open.

*Petalage.*—250 to 300 Ray petals. 4 to 6 Disc Petals.

*Color of open bloom.*—Inner face of fully expanded petal R.H.S. 155C. Outer face of fully expanded petal R.H.S. 155C.

*Response group.*—9 weeks.

*Temperature tolerance.*—13° C.-18° C. (56° F.-65° F.) at night.

*Plant.*—Strong upright habit of growth, medium vigor.

*Foliage.*—Good quality with average internode length of 4 cm; medium size and medium texture, rounded; color R.H.S. 133A.

*Stem.*—Upright, medium thickness and strong. Color R.H.S. 131A at flowering.

*Water uptake.*—Good.

I claim:

1. A new and distinct variety of *Chrysanthemum morifolium* bailey of the white spray type substantially as herein shown and described, characterized particularly as to novelty by a long flowering season, fast response, vigorous growth, and non-susceptibility to tip scorch/loss.

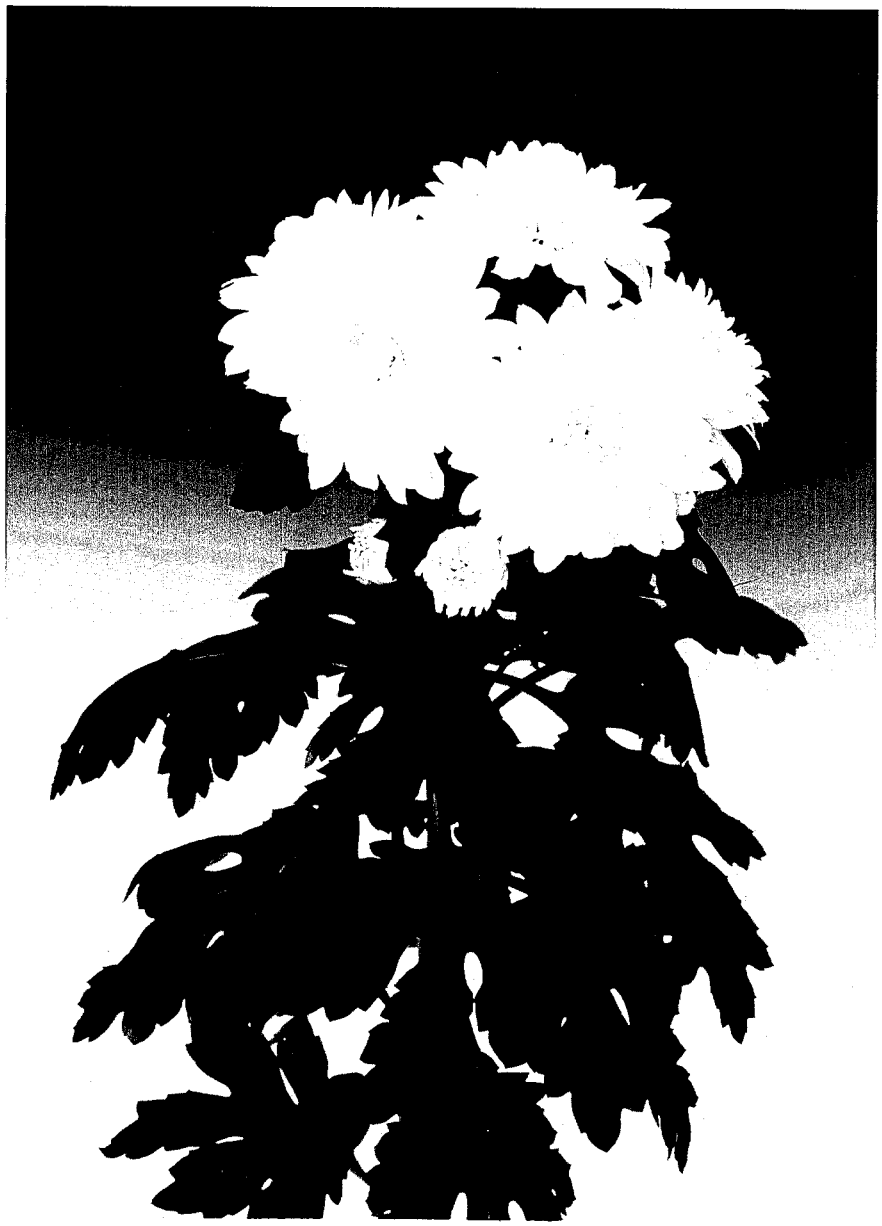

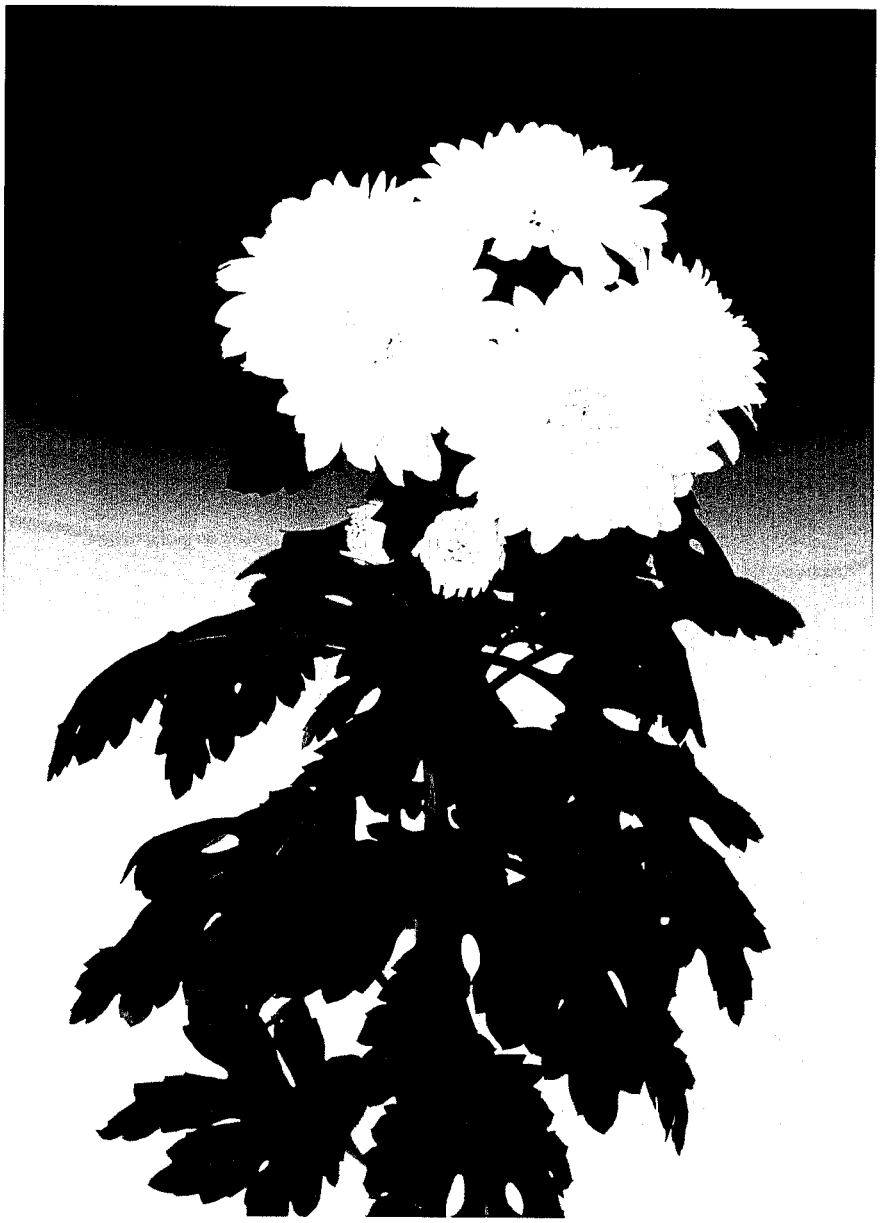

* * * * *